United States Patent
Parvulescu et al.

(10) Patent No.: US 11,110,442 B2
(45) Date of Patent: Sep. 7, 2021

(54) PROCESS FOR PREPARING A MOLDING COMPRISING ZINC AND A TITANIUM-CONTAINING ZEOLITE

(71) Applicant: BASF SE, Ludwigshafen am Rhein (DE)

(72) Inventors: Andrei-Nicolae Parvulescu, Ludwigshafen (DE); Ulrich Mueller, Ludwigshafen (DE); Hans-Juergen Luetzel, Ludwigshafen (DE); Joaquim Henrique Teles, Ludwigshafen (DE); Dominic Riedel, Ludwigshafen (DE); Daniel Urbanczyk, Ludwigshafen (DE); Ulrike Wegerle, Worms (DE); Markus Weber, Ludwigshaven (DE); Nicolai Tonio Woerz, Ludwigshafen (DE); Christian Mueller, Ludwigshafen (DE)

(73) Assignee: BASF SE

( * ) Notice: Subject to any disclaimer, the term of this patent is extended or adjusted under 35 U.S.C. 154(b) by 0 days.

(21) Appl. No.: 16/997,038

(22) Filed: Aug. 19, 2020

(65) Prior Publication Data

US 2020/0376472 A1 Dec. 3, 2020

Related U.S. Application Data

(63) Continuation of application No. 16/470,834, filed as application No. PCT/EP2018/051168 on Jan. 18, 2018, now Pat. No. 10,780,432.

(30) Foreign Application Priority Data

Jan. 18, 2017 (EP) .................................... 17151943

(51) Int. Cl.
| | | |
|---|---|---|
| *B01J 29/89* | (2006.01) | |
| *B01J 29/70* | (2006.01) | |
| *B01J 35/02* | (2006.01) | |
| *B01J 35/10* | (2006.01) | |
| *B01J 37/00* | (2006.01) | |
| *B01J 37/08* | (2006.01) | |
| *C01B 39/02* | (2006.01) | |
| *C01B 39/06* | (2006.01) | |
| *C01B 39/12* | (2006.01) | |
| *C07D 301/12* | (2006.01) | |

(52) U.S. Cl.
CPC ........... *B01J 29/89* (2013.01); *B01J 29/7088* (2013.01); *B01J 35/023* (2013.01); *B01J 35/1019* (2013.01); *B01J 35/1042* (2013.01); *B01J 37/0045* (2013.01); *B01J 37/08* (2013.01); *C01B 39/026* (2013.01); *C07D 301/12* (2013.01); *B01J 2229/183* (2013.01); *B01J 2229/42* (2013.01)

(58) Field of Classification Search
CPC ...... B01J 29/89; B01J 29/7088; B01J 35/023; B01J 35/1019; B01J 35/1042; B01J 37/0045; B01J 37/08; B01J 2229/183; B01J 2229/42; B01J 2229/186; B01J 2229/34; B01J 2229/37; B01J 2229/40; C01B 39/026; C01B 39/065; C01B 39/12; C07D 301/12

See application file for complete search history.

(56) References Cited

U.S. PATENT DOCUMENTS

| 3,879,519 A | 4/1975 | Woodell |
| 2015/0368115 A1 | 12/2015 | Parvulescu et al. |

FOREIGN PATENT DOCUMENTS

| CN | 105854933 A | 8/2016 |
| RU | 2332409 C2 | 8/2008 |
| WO | 2004/099166 A1 | 11/2004 |
| WO | WO 2013/117536 A2 | 8/2013 |
| WO | WO 2015/010990 A1 | 1/2015 |

OTHER PUBLICATIONS

International Search Report and Written Opinion of the International Searching Authority dated Apr. 26, 2018 in PCT/EP2018/051168 filed Jan. 18, 2018, citing documents AA, AP and AQ therein, 16 pages.
International Preliminary Report on Patentability dated Aug. 1, 2019 in PCT/EP2018/051168 filed Jan. 18, 2018, citing documents AA, AP and AQ therein, 10 pages.
"Respublika Baskortostan", 2017., str. 8-10 (= Suundukov A. T. et al., Use of natural zeolites of Trans-Urals Bashkortostan for improving soil productivity and crop yield (recommendation for production), Sibaj, SIC—branch office of State Unitary Enterprise of Republic of Bashkortostan Publishing house "Republic Bashkortostan", 2017, pp. 8-10).
I.M. Kolesnikov. Kataliz v gazoneftanoj otrasli.—Moskva—2012 (= I.M. Kolesnikov. Katalysis in gas-oil field. —Moscow—2012), Suundukov A. T. i dr., Ispol'zovanie prirodnyh ceolitov Zaural'a Baskortostana dla povysenia plodorodia pocv ii urozajnosti sel'skohozajstvennyh kultur (rekomendacii proizvodstvu), Sibaj, SIC—filial GUP RB Izdatel'skij dom.

*Primary Examiner* — John M Mauro
(74) *Attorney, Agent, or Firm* — Faegre Drinker Biddle & Reath LLP

(57) ABSTRACT

A process for preparing a molding comprising zinc and a titanium-containing zeolitic material having framework type MWW, comprising (i) providing a molding comprising a titanium-containing zeolitic material having framework type MWW; (ii) preparing an aqueous suspension comprising a zinc source and the molding comprising a titanium-containing zeolitic material having framework type MWW prepared in (i); (iii) heating the aqueous suspension prepared in (ii) under autogenous pressure to a temperature of the liquid phase of the aqueous suspension in the range of from 100 to 200° C., obtaining an aqueous suspension comprising a molding comprising zinc and a titanium-containing zeolitic material having framework type MWW; (iv) separating the molding comprising zinc and a titanium-containing zeolitic material having framework type MWW from the liquid phase of the suspension obtained in (iii).

16 Claims, No Drawings

PROCESS FOR PREPARING A MOLDING COMPRISING ZINC AND A TITANIUM-CONTAINING ZEOLITE

This is a continuation of application Ser. No. 16/470,834, filed Jun. 18, 2019, which is the National Stage of International application no. PCT/EP2018/051168, filed Jan. 18, 2018, which claims priority to European patent application no. 17151943.2, filed Jan. 18, 2017, of which all of the disclosures are incorporated herein by reference in their entireties.

The present invention is directed to a process for preparing a molding which comprises zinc and a titanium-containing zeolitic material wherein the zeolitic framework structure of the zeolitic material has framework type MWW. Further, the present invention relates to a molding which is obtainable or obtained by said process, and further relates to the use of said molding as a catalyst.

TiMWW catalysts, for example a ZnTiMWW catalyst, i.e. catalysts comprising a titanium-containing zeolitic material having framework type MWW which further comprises zinc, are known as excellent catalysts for the epoxidation of propene. Such catalysts are usually prepared in a synthesis process involving a shaping stage such as an extrusion step where moldings are prepared which are preferred for catalysts used in industrial-scale processes such as the above-mentioned epoxidation process. Usually, the process for preparing the moldings, i.e. the shaping process, starts from a zeolitic material which comprises zinc. A process for preparing such moldings is disclosed, for example, in WO 2013/117536 A from which process catalysts are obtained which, with regard to a preferred use, i.e. the use as an epoxidation catalyst, exhibit most excellent characteristics. As described in WO 2013/117536 A, the process is a multi-stage process wherein the shaping process is based on a powder material of a zeolitic material which comprises zinc. Thus, the shaping process is preferably designed based on the characteristics of said powder material.

Thus, although the catalysts described in WO 2013/117536 A exhibit excellent characteristics, there was a need to provide a shaping process which is applicable for a whole variety of titanium-containing zeolitic materials having framework type MWW. Further, there was a certain desire to provide a process which is even more economic than the process described in WO 2013/117536 A. Surprisingly, it was found that it is possible to incorporate zinc in the molding during the shaping step and arrive at a catalyst having the same or even improved properties compared with the moldings of WO 2013/117536 A when used, for example, as an epoxidation catalyst. It was further found that by doing so, it was possible to eliminate one step of the multistage process of WO 2013/117536 A thus rendering the overall process more economic which is a highly advantageous feature of a preparation process in particular in a technical field where the respectively obtained product is a commercial product used in an industrial-scale process, as it is the case, for example, for epoxidation catalysts.

Therefore, the present invention relates to a process for preparing a molding comprising zinc and a titanium-containing zeolitic material having framework type MWW, comprising (i) providing a molding comprising a titanium-containing zeolitic material having framework type MWW;
(ii) preparing an aqueous suspension comprising a zinc source and the molding comprising a titanium-containing zeolitic material having framework type MWW prepared in (i);
(iii) heating the aqueous suspension prepared in (ii) under autogenous pressure to a temperature of the liquid phase of the aqueous suspension in the range of from 100 to 200° C., obtaining an aqueous suspension comprising a molding comprising zinc and a titanium-containing zeolitic material having framework type MWW;
(iv) separating the molding comprising zinc and a titanium-containing zeolitic material having framework type MWW from the liquid phase of the suspension obtained in (iii).

Step (i)

Generally, the molding provided in (i) may consist of the titanium-containing zeolitic material having framework type MWW. Preferably, the molding comprises, in addition to the titanium-containing zeolitic material having framework type MWW, a binder. In addition to the binder and the titanium-containing zeolitic material having framework type MWW, the molding may comprise one or more further additional components. Preferably at least 90 weight-%, more preferably at least 95 weight-%, more preferably at least 99 weight-%, more preferably at least 99.9 weight-% of the molding provided in (i) consist of the titanium-containing zeolitic material having framework type MWW and the binder. More preferably, apart from any impurities which may be comprised in the binder and/or the titanium-containing zeolitic material having framework type MWW, the molding comprises no further component, and therefore, it is preferred that the molding essentially consists of, more preferably consists of, the binder and the titanium-containing zeolitic material having framework type MWW. In the molding provided in (i), the weight ratio of the titanium-containing zeolitic material having framework type MWW relative to the binder is not subject to any specific restrictions. For example, the weight ratio may be in the range of from 0.01:1 to 100:1 or from 0.1:1 to 10:1. Preferably, the weight ratio is in the range of from 1:1 to 9:1, more preferably in the range of from 2:1 to 7:1, more preferably in the range of from 3:1 to 5:1. While the chemical nature of the binder is not subject to any specific restrictions, it is preferred that the binder comprises, more preferably is, a silica binder.

Therefore, it is preferred that at least 99.9 weight-% of the molding provided in (i) consist of the titanium-containing zeolitic material having framework type MWW and a silica binder.

The geometry of the molding provided in (i) is not subject to any specific restrictions. Preferably, the molding provided in (i) is in the form of a tablet, a sphere, a cylinder, a star, a strand, or a trilob, wherein the molding is preferably a strand, more preferably an extrudate strand, preferably having rectangular, triangular hexagonal, quadratic, oval, or circular cross-section. The diameter of the preferred circular cross-section is preferably in the range of from 0.2 to 5.0 mm, more preferably in the range of from 0.5 to 3.5 mm, more preferably in the range of from 1.0 to 2.0 mm.

Preferably, the molding provided in (i) is a calcined molding, wherein the calcination is preferably a calcination carried out in at a gas atmosphere at a temperature of the gas atmosphere preferably in the range of from 350 to 650° C., more preferably in the range of from 400 to 600° C., more preferably in the range of from 450 to 550° C., wherein a preferred gas atmosphere comprises air, lean air, or nitrogen such as technical nitrogen, more preferably air.

Preferably, the molding provided in (i) exhibits one or more of the following characteristics (1) to (3), preferably two or more of the following characteristics (1) to (3), more preferably the following characteristics (1) to (3):

(1) a BET specific surface area of at least 300 m²/g determined as described in Reference Example 1 herein;
(2) a pore volume of at least 0.9 mL/g, determined as described in Reference Example 2 herein;
(3) a mechanical strength in the range of from 5 to 10 N, preferably in the range of from 6 to 9 N, determined as described in Reference Example 3 herein.

Therefore, it is preferred that at least 99.9 weight-% of the molding provided in (i) consist of the titanium-containing zeolitic material having framework type MWW and a silica binder, wherein the molding exhibits the characteristics (1) to (3) described above.

There are no specific restrictions how the molding provided in (i) is prepared. A preferred process for the preparation of the molding comprises (i.1) preparing a mixture comprising the titanium-containing zeolitic material having framework type MWW, a binder or a source of a binder, a pasting agent and optionally a pore-forming agent;
(i.2) shaping the mixture prepared in (i.1), obtaining a molding comprising the titanium-containing zeolitic material having framework type MWW and a binder or a source of a binder:
(i.3) drying the molding obtained in (i.2);
(i.4) calcining the dried molding obtained in (i.3), obtaining the molding comprising the titanium-containing zeolitic material having framework type MWW and a binder.

Preferably, the pasting agent according to (i) comprises one or more of water and a hydrophilic polymer, more preferably one or more of water and a carbohydrate, more preferably water and a carbohydrate. The carbohydrate preferably comprises, more preferably is, one or more of a cellulose and a cellulose derivative, more preferably comprises, more preferably is, one or more of a cellulose, a cellulose ether and a cellulose ester, more preferably comprises, more preferably is, a cellulose ether, more preferably a cellulose alkyl ether, more preferably a methyl cellulose. Therefore, it is preferred that the pasting agent according to (i.1) comprises, more preferably is, water and a methyl cellulose.

If the mixture prepared in (i.1) comprises a pore-forming agent, it is preferred that the pore-forming agent comprises, preferably is, a mesopore-forming agent, which is preferably one or more of a polyalkylene oxide such as polyethylene oxide, a polystyrene, a poly-acrylate, a polymethacrylate, a polyolefin, a polyamide, and a polyester. Polyethylene oxide may be preferred, wherein the may have a mean molecular weight MW (g/mol) in the range of from 100,000 to 6,000,000, such as of about 4,000,000.

Preferably, the binder or precursor of a binder of the mixture provided in (i.1) comprises, more preferably is, a silica binder or a precursor of a silica binder. Regarding the precursor of the silica binder, it is generally possible to use both colloidal silica and so-called "wet process" silica and so-called "dry process" silica. Particularly preferably this silica is amorphous silica, the size of the silica particles being, for example, in the range of from 1 to 100 nm and the surface area of the silica particles being in the range of from 50 to 500 m²/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as HiSil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Preferably according to the present invention, the precursor of the silica binder comprised in the mixture according to (i.1) comprises, more preferably is, one or more of a silica gel, a precipitated silica, a fumed silica, and a colloidal silica. More preferably, the precursor of the silica binder comprised in the mixture according to (i.1) comprises, preferably is, a colloidal silica. More preferably, the precursor of the silica binder comprised in the mixture according to (i.1) consists of a colloidal silica, wherein more preferably, the silica binder or the precursor comprises, preferably is, a colloidal silica.

Preferably, in the mixture prepared in (i.1), the weight ratio of the titanium-containing zeolitic material having framework type MWW relative to the silica comprised in the binder or the precursor of the binder is in the range of from 1:1 to 9:1, more preferably in the range of from 2:1 to 7:1, more preferably in the range of from 3:1 to 5:1.

Preferably, the mixture prepared in (i.1) does not comprise zinc, neither in the binder nor in the titanium-containing zeolitic material having framework type MWW nor in any other components of the mixture. The term "does not contain zinc" does not exclude a minimum amount of zinc which may be present in the mixture due to impurities in one or more components of the mixture which cannot be avoided.

Preferably at least 99 weight-%, preferably at least 99.5 weight-%, more preferably at least 99.9 weight-% of the mixture prepared in (i.1) consist of the titanium-containing zeolitic material having framework type MWW, the binder or the precursor of the binder, and the pasting agent.

Preferably, preparing the mixture according to (i.1) comprises mechanically agitating, more preferably kneading the mixture, wherein the kneading is preferably carried out until the individual components of the mixture which were added in a suitable sequence together form a homogenous mass.

Preferably, shaping according to (i.2) comprises extruding the mixture prepared in (i.1). Regarding the extruding according to (i.2), no specific restrictions exist. Generally, every method of extruding the mixture obtained from (i.1) can be employed. The term "extrusion" as used herein relates to a method from which moldings having an essentially fixed cross-sectional profile are obtained wherein the composition obtained from (iv) is suitably pushed through a suitable die which exhibits the desired cross-section. The molding which is obtained from the extruder used can be cut downstream of the respectively used die, for example using a suitable air stream and/or a mechanical cutting device such as a suitable wire. If it is not necessary to obtain moldings having essentially identical length, it is also possible that the molding obtained from the extruder is not cut but breaks under its own weight downstream of the die leading to moldings having different lengths. The cross-section of the molding can be, for example, circle-shaped, oval, star-shaped, and the like. Preferably, according to the present invention, the molding has a circle-shaped cross-section wherein the diameter is preferably in the range of from 0.2 to 5.0 mm, more preferably in the range of from 0.5 to 3.5 mm, more preferably in the range of from 1.0 to 2.0 mm.

Preferably, according to (i.3), the molding is dried. The drying is preferably carried out in a gas atmosphere at a temperature of the gas atmosphere preferably in the range of from 80 to 200° C., more preferably in the range of from 90 to 175° C., more preferably in the range of from 100 to 150° C. Every suitable gas atmosphere can be used wherein a preferred gas atmosphere comprises air, lean air, or nitrogen such as technical nitrogen.

Preferably, according to (i.4), the dried molding obtained from (i.3) is calcined. The calcination is preferably carried out in at a gas atmosphere at a temperature of the gas atmosphere preferably in the range of from 350 to 650° C., more preferably in the range of from 400 to 600° C., more preferably in the range of from 450 to 550° C. Every suitable gas atmosphere can be used wherein a preferred gas atmosphere comprises air, lean air, or nitrogen such as technical nitrogen.

Regarding the titanium-containing zeolitic material having framework type MWW comprised in the molding provided in (i), no specific restrictions exist with regard to is chemical composition. Therefore, it may be possible that in addition to Ti, Si, O and H, the zeolitic material contains further framework and/or extra-framework elements for example one or more three-valent, one or more tetra-valent, and/or one or more penta-valent framework elements such as Al, In, Ga, B, Ge, Sn, and the like. Preferably, at least 95 weight-%, more preferably at least 98 weight-%, more preferably at least 99 weight-% of the titanium-containing zeolitic material having framework type MWW comprised in the molding provided in (i) consist of Ti, Si, O, and H wherein the framework of the zeolitic material preferably essentially consists of Ti, Si and O. The titanium content of the titanium-containing zeolitic material having framework type MWW comprised in the molding provided in (i) is not subject to any specific restrictions. Preferably, the titanium-containing zeolitic material having framework type MWW comprised in the molding provided in (i) has a titanium content, calculated as elemental titanium, in the range of from 0.1 to 5 weight-%, more preferably in the range of from 0.5 to 3 weight-%, more preferably in the range of from 1 to 3 weight-%, based on the total weight of the titanium-containing zeolitic material having framework type MWW. A preferred range may be of from 1.5 to 2 weight-%. Preferably, the titanium-containing zeolitic material having framework type MWW comprised in the molding provided in (i) has a silicon content, calculated as elemental silicon, in the range of from 30 to 60 weight-%, preferably in the range of from 35 to 55 weight-%, more preferably in the range of from 40 to 50 weight-%, more preferably in the range of from 1 to 3 weight-%, based on the total weight of the titanium-containing zeolitic material having framework type MWW. A preferred range may be of from 44 to 48 weight-%. Therefore, it is preferred that the titanium-containing zeolitic material having framework type MWW comprised in the molding provided in (i) has a titanium content in the range of from 1 to 3 weight-% and a silicon content in the range of from 40 to 50 weight-%, wherein it may be preferred that it has a titanium content in the range of from 1.5 to 2 weight-% and a silicon content in the range of from 44 to 48 weight-%.

Preferably, the titanium-containing zeolitic material having framework type MWW comprised in the molding provided in (i) has a total organic carbon content of at most 0.1 weight-%, based on the total weight of the titanium-containing zeolitic material having framework type MWW. Preferably, the titanium-containing zeolitic material having framework type MWW comprised in the molding provided in (i) has a boron content, calculate as elemental boron, of at most 0.1 weight-% or at most 0.5 weight-%, more preferably of at most 0.5 weight %, based on the total weight of the titanium-containing zeolitic material having framework type MWW. Preferably, the titanium-containing zeolitic material having framework type MWW comprised in the molding provided in (i) has a BET specific surface area of at least 400 m$^2$/g, preferably in the range of from 400 to 600 m$^2$/g, more preferably in the range of from 450 to 550 m$^2$/g, wherein the BET specific surface area is determined as described in Reference Example 1 herein. Preferably, the titanium-containing zeolitic material having framework type MWW comprised in the molding provided in (i) has a crystallinity of at least 70%, preferably in the range of from 70 to 90%, more preferably in the range of from 70 to 80%, wherein the crystallinity is determined as described in Reference Example 4 herein. Preferably, the titanium-containing zeolitic material having framework type MWW comprised in the molding provided in (i) is in the form of a powder having a particle size distribution characterized by a Dv10 value in the range of from 1 to 10 micrometer, preferably in the range of from 1.5 to 10 micrometer, more preferably in the range of from 2 to 6 micrometer, a Dv50 value in the range of from 5 to 50 micrometer, preferably in the range of from 7 to 50 micrometer, more preferably in the range of from 8 to 30 micrometer, and a Dv90 value in the range of from 12 to 200 micrometer, preferably in the range of from 12 to 90 micrometer, more preferably in the range of from 13 to 70 micrometer, wherein the particle size distribution is determined as described in Reference Example 5 herein. The titanium-containing zeolitic material having framework type MWW comprised in the molding provided in (i) may be a spray powder, i.e. a powder obtained from a spray-drying process, or may be powder which is obtained from other processes which may result in a powder having the above-mentioned preferred particle size distribution, such as flash drying or may be microwave drying.

According to preferred embodiments of the present invention, the titanium-containing zeolitic material having framework type MWW comprised in molding prepared in (i), for example comprised in the mixture prepared in (i.1), is obtainable or obtained by a process comprising (a) preparing a boron-containing zeolitic material having framework type MWW, wherein at least 99 weight-% of the zeolitic framework consist of B, Si, O and H;

(b) deboronating the boron-containing zeolitic material having framework type MWW prepared in (a), obtaining a deboronated zeolitic material having framework type MWW, wherein at least 99 weight-% of the zeolitic framework of the deboronated zeolitic material consist of B, Si, O and H, and wherein the zeolitic framework of the deboronated zeolitic material has empty framework sites;

(c) incorporating titanium into the deboronated zeolitic material obtained from (b), comprising preparing an aqueous synthesis mixture containing the deboronated zeolitic material obtained from (b), a titanium source, and an MWW template compound; and hydrothermally synthesizing a titanium-containing zeolitic material having framework type MWW from the aqueous synthesis mixture prepared in (c), obtaining a mother liquor comprising a titanium-containing zeolitic material having framework type MWW;

(d) separating the titanium-containing zeolitic material having framework type MWW synthesized in (c) from the mother liquor;

(e) treating the separated titanium-containing zeolitic material having framework type MWW obtained from (d) with an aqueous solution having a pH of at most 5;

(f) separating the titanium-containing zeolitic material having framework type MWW obtained from (e) from the aqueous solution, optionally followed by washing the separated the titanium-containing zeolitic material having framework type MWW;

(g) preparing a suspension, preferably an aqueous suspension, containing the titanium-containing zeolitic material having framework type MWW obtained from (f), and subjecting the suspension to spray-drying;
(h) calcining the titanium-containing zeolitic material having framework type MWW obtained from (g).

According to a preferred embodiment of the present invention, providing the titanium-containing zeolitic material having framework type MWW comprised in molding prepared in (i) comprises
(a) preparing a boron-containing zeolitic material having framework type MWW, wherein at least 99 weight-% of the zeolitic framework consist of B, Si, O and H;
(b) deboronating the boron-containing zeolitic material having framework type MWW prepared in (a), obtaining a deboronated zeolitic material having framework type MWW, wherein at least 99 weight-% of the zeolitic framework of the deboronated zeolitic material consist of B, Si, O and H, and wherein the zeolitic framework of the deboronated zeolitic material has empty framework sites;
(c) incorporating titanium into the deboronated zeolitic material obtained from (b), comprising preparing an aqueous synthesis mixture containing the deboronated zeolitic material obtained from (b), a titanium source, and an MWW template compound; and hydrothermally synthesizing a titanium-containing zeolitic material having framework type MWW from the aqueous synthesis mixture prepared in (c), obtaining a mother liquor comprising a titanium-containing zeolitic material having framework type MWW;
(d) separating the titanium-containing zeolitic material having framework type MWW synthesized in (c) from the mother liquor;
(e) treating the separated titanium-containing zeolitic material having framework type MWW obtained from (d) with an aqueous solution having a pH of at most 5;
(f) separating the titanium-containing zeolitic material having framework type MWW obtained from (e) from the aqueous solution, optionally followed by washing the separated the titanium-containing zeolitic material having framework type MWW;
(g) preparing a suspension, preferably an aqueous suspension, containing the titanium-containing zeolitic material having framework type MWW obtained from (f), and subjecting the suspension to spray-drying;
(h) calcining the titanium-containing zeolitic material having framework type MWW obtained from (g).

According to a preferred embodiment of the present invention, preparing the boron-containing zeolitic material having framework type MWW in (a) comprises
(a.1) preparing an aqueous synthesis mixture comprising a silicon source, a boron source, and an MWW template compound;
(a.2) hydrothermally synthesizing a precursor of the boron-containing zeolitic material having framework type MWW from the aqueous synthesis mixture prepared in (a.1), obtaining a mother liquor comprising the precursor of the boron-containing zeolitic material having framework type MWW;
(a.3) separating the precursor of the boron-containing zeolitic material having framework type MWW from the mother liquor, obtaining the separated precursor of the boron-containing zeolitic material having framework type MWW;
(a.4) calcining the separated precursor of the boron-containing zeolitic material having framework type MWW, obtaining the boron-containing zeolitic material having framework type MWW.

In the aqueous synthesis mixture prepared in (a.1), the molar ratio of the MWW template compound relative to Si, calculated as elemental silicon and comprised in the silicon source, is preferably at least 0.4.1, more preferably in the range of from 0.4:1 to 2.0:1, more preferably in the range of from 0.6:1 to 1.9:1, more preferably in the range of from 0.9:1 to 1.4:1. In the aqueous synthesis mixture prepared in (a.1), the molar ratio of water relative to the silicon source, calculated as elemental silicon, is preferably in the range of from 1:1 to 30:1, more preferably in the range of from 3:1 to 25:1, more preferably in the range of from 6:1 to 20:1. In the aqueous synthesis mixture prepared in (a.1), the molar ratio of the boron source, calculated as elemental boron, relative to the silicon source, calculated as elemental silicon, is preferably in the range of from 0.4:1 to 2.0:1, more preferably in the range of from 0.6:1 to 1.9:1, more preferably in the range of from 0.9:1 to 1.4:1. In (a.1), the boron source is preferably one or more of boric acid, a borate, and boron oxide, more preferably boric acid. In (a.1), the silicon source is preferably one or more of fumed silica and colloidal silica, more preferably colloidal silica, more preferably ammonia-stabilized colloidal silica. In (a.1), the MWW template compound is preferably one or more of piperidine, hexamethylene imine, N,N,N,N',N',N'-hexamethyl-1,5-pentanediammonium ion, 1,4-bis(N-methylpyrrolidini-um)butane, octyltrimethylammonium hydroxide, heptyltrimethylammonium hydroxide, and hexyltrimethylammonium hydroxide, more preferably piperidine. Preferably at least 99 weight-%, more preferably at least 99.5 weight-%, more preferably at least 99.9 weight-% of the aqueous synthesis mixture prepared in (a.1) consist of water, the boron source, the silicon source, and the MWW template compound.

In (a.2), the hydrothermally synthesizing is carried out at a temperature of the aqueous synthesis mixture preferably in the range of from 160 to less than 180° C., more preferably in the range of from 170 to 177° C. In (a.2), the hydrothermally synthesizing is carried out for a period of time preferably in the range of from 1 to 72 h, more preferably in the range of from 6 to 60 h, more preferably in the range of from 12 to 50 h. In (a.2), the hydrothermally synthesizing is preferably carried out in a closed system under autogenous pressure. The pH of the mother liquor obtained in (a.2) is preferably greater than 10, more preferably at least 10.5, more preferably at least 11, and after (a.2) and before (a.3), the pH of the mother liquor is preferably adjusted to a value of at most 10, more preferably at most 9, more preferably at most 8, more preferably in the range of from 7 to 8. Preferably, the pH of the liquid phase of the mother liquor is adjusted by subjecting the liquid phase of the mother liquor to an acid treatment, wherein the acid is preferably an inorganic acid, more preferably one or more of phosphoric acid, sulphuric acid, hydrochloric acid, and nitric acid, the acid more preferably being nitric acid.

The separating according to (a.3) preferably comprises subjecting the mother liquor obtained in (a.2) to filtration. The separating according to (a.3) preferably comprises drying, preferably spray-drying.

In (a.4), the separated precursor of the boron-containing zeolitic material having framework type MWW is calcined at a temperature preferably in the range of from 400 to 800° C., more preferably from 600 to 700° C.

In (b), the boron-containing zeolitic material having framework type MWW prepared in (a) is preferably deboronated by treating the boron-containing zeolitic material having framework type MWW with a liquid solvent system, obtaining the deboronated zeolitic material having framework type MWW, wherein preferably at least 99 weight-% of the zeolitic framework of the deboronated zeolitic material consist of B, Si, O and H and wherein the zeolitic framework of the deboronated zeolitic material preferably has empty framework sites. Preferably, the deboronated zeolitic material having framework type MWW obtained from (b) has a molar ratio of boron, calculated as $B_2O_3$, relative to silicon, calculated as $SiO_2$, of at most 0.02:1, more preferably at most 0.01:1, more preferably in the range of from 0.001:1 to 0.01:1, more preferably in the range of from 0.001:1 to 0.003:1, wherein preferably at least 99.5 weight-%, more preferably least 99.9 weight-% of the deboronated zeolitic material having framework type MWW consist of B, Si, O and H. In (b), the liquid solvent system is preferably one or more of water, methanol, ethanol, propanol, ethane-1,2-diol, propane-1,2-diol, propane-1,3-diol, and propane-1,2,3-triol, wherein preferably, the liquid solvent system does not contain an inorganic acid and an organic acid. Prior to (b), the weight ratio of the liquid solvent system relative to the zeolitic material having framework type MWW is preferably in the range of from 5:1 to 40:1, more preferably in the range of from 7.5:1 to 30:1, more preferably in the range of from 10:1 to 20:1. In (b), the treating with the liquid solvent system is preferably carried out at a temperature of the liquid solvent system in the range of from 50 to 125° C., more preferably in the range of from 90 to 115° C., more preferably in the range of from 95 to 105° C. In (b), the treating with the liquid solvent system is preferably carried out for a period in the range of from 6 to 20 h, more preferably in the range of from 7 to 17 h, more preferably in the range of from 8 to 12 h. In (b), the treating with the liquid solvent system is preferably carried out in an open system under reflux or in a closed system without reflux. Preferably, (b) comprises drying, more preferably spray-drying the deboronated zeolitic material having framework type MWW. Preferably, the deboronated zeolitic material having framework type MWW obtained from (b) is not subjected to calcination prior to (c).

In (c), the MWW template compound is preferably one or more of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, and hexyltrimethylammonium hydroxide, more preferably piperidine. In (c), the titanium source is preferably one ore more of tetra-n-butyl orthotitanate, tetraiso-propyl orthotitanate, tetraethyl orthotitanate, titanium dioxide, titanium tetrachloride, and titanium tert-butoxide, the titanium source preferably being tetra-n-butyl orthotitanate. In the aqueous synthesis mixture in (c), the molar ratio of Ti, calculated as $TiO_2$ and comprised in the titanium source, relative to Si, calculated as $SiO_2$ and comprised in the deboronated zeolitic material having framework type MWW, is preferably in the range of from 0.005:1 to 0.1:1, more preferably the range of from 0.01:1 to 0.08:1, more preferably the range of from 0.02:1 to 0.06:1, the molar ratio of $H_2O$ relative to Si, calculated as $SiO_2$ and comprised in the deboronated zeolitic material having framework type MWW, is preferably in the range of from 8:1 to 20:1, more preferably the range of from 10:1 to 18:1, more preferably the range of from 12:1 to 16:1, and the molar ratio of the MWW template compound relative to Si, calculated as $SiO_2$ and comprised in deboronated zeolitic material having framework type MWW, is preferably in the range of from 0.5:1 to 1.7:1, more preferably the range of from 0.8:1 to 1.5:1, more preferably the range of from 1.0:1 to 1.3:1. In (c), the hydrothermal synthesizing is preferably carried out at a temperature in the range of from 80 to 250° C., more preferably the range of from 120 to 200° C., more preferably the range of from 160 to 180° C., preferably in a closed system under autogenous pressure. Preferably, neither during (c), nor after (c) and before (d), the titanium-containing zeolitic material having framework type MWW is separated from its mother liquor.

Preferably, the mother liquor subjected to (d) comprising the titanium-containing zeolitic material having framework type MWW has a solids content, optionally after concentration or dilution, in the range of from 5 to 25 weight-%, more preferably in the range of from 10 to 20 weight-%, based on the total weight of the mother liquor comprising the titanium-containing zeolitic material having framework type MWW. Preferably, the separating according to (d) comprises spray-drying, wherein during spray-drying in (d), the drying gas inlet temperature is preferably in the range of from 200 to 700° C., preferably in the range of from 200 to 350° C., and the drying gas outlet temperature is preferably in the range of from 70 to 190° C.

In (e), the weight ratio of the aqueous solution relative to the titanium-containing zeolitic material having framework type MWW is preferably in the range of from 10:1 to 30:1, more preferably in the range of from 15:1 to 25:1, more preferably in the range of from 18:1 to 22:1, and the aqueous solution preferably comprises an inorganic acid, more preferably one or more of phosphoric acid, sulphuric acid, hydrochloric acid, and nitric acid, more preferably nitric acid. Preferably, after (d) and before (e), the separated the titanium-containing zeolitic material having framework type MWW obtained from (d) is not subjected to calcination. In (e), the aqueous solution preferably has a pH in the range of from 0 to 5, more preferably in the range of from 0 to 3, more preferably in the range of from 0 to 2. In (e), the titanium-containing zeolitic material having framework type MWW is preferably treated with the aqueous solution at a temperature of the aqueous solution in the range of from 50 to 175° C., more preferably in the range of from 70 to 125° C., more preferably in the range of from 95 to 105° C., preferably in a closed system under autogenous pressure.

The separating of the titanium-containing zeolitic material having framework type MWW according to (f) preferably comprises washing the titanium-containing zeolitic material having framework type MWW. The separating of the titanium-containing zeolitic material having framework type MWW according to (f) preferably comprises drying the titanium-containing zeolitic material having framework type MWW. The separating of the titanium-containing zeolitic material having framework type MWW according to (f) preferably comprises preparing a suspension, preferably an aqueous suspension containing the titanium-containing zeolitic material having framework type MWW obtained from (e), said suspension having a solids content preferably in the range of from 5 to 25 weight-%, more preferably in the range of from 10 to 20 weight-%, based on the total weight of the suspension, and subjecting the suspension to spray-drying. During spray-drying, the drying gas inlet temperature is preferably in the range of 200 to 700° C., more preferably in the range of from 200 to 330° C., and the drying gas outlet temperature is preferably in the range of from 100 to 180° C., more preferably in the range of from 120 to 180° C.

The calcining in (h) is preferably carried out at a temperature in the range of from 400 to 800° C., more preferably in the range of from 600 to 700° C.

Step (ii)

Generally, there are no specific restrictions regarding the chemical nature of the zinc source used according to (ii). Preferably, the zinc source comprises, more preferably consists of, a zinc compound which is soluble in water, preferably at the temperature and pressure of the liquid aqueous phase according to (iii). More preferably, the zinc source comprises one or more of a zinc salt of an organic or inorganic acid, preferably comprises one or more of zinc acetate, zinc benzoate, zinc borate, zinc bromide, zinc chloride, zinc formate, zinc gluconate, zinc lactate, zinc laurate, zinc malate, zinc nitrate, zinc perborate, zinc sulfate, zinc sulfamate, zinc tartrate, more preferably comprises zinc acetate, more preferably comprises zinc acetate dihydrate. More preferably, the zinc source consists of one or more of a zinc salt of an organic or inorganic acid, preferably consists of one or more of zinc acetate, zinc benzoate, zinc borate, zinc bromide, zinc chloride, zinc formate, zinc gluconate, zinc lactate, zinc laurate, zinc malate, zinc nitrate, zinc perborate, zinc sulfate, zinc sulfamate, zinc tartrate, more preferably consists of zinc acetate, more preferably consists of zinc acetate dihydrate.

In the aqueous suspension prepared in (ii), the weight ratio of zinc, calculated as elemental zinc and comprised in the zinc source relative to the titanium-containing zeolitic material having framework type MWW comprised in the molding is preferably in the range of from 0.005:1 to 0.1:1, more preferably in the range of from 0.01:1 to 0.075:1, more preferably in the range of from 0.02:1 to 0.05:1, more preferably in the range of from 0.03:1 to 0.04:1. Further in the aqueous suspension prepared in (ii), the weight ratio of the titanium-containing zeolitic material having framework type MWW comprised in the molding relative to water is preferably in the range of from 0.01:1 to 0.1:1, more preferably in the range of from 0.02:1 to 0.075:1, more preferably in the range of from 0.03:1 to 0.05:1.

Generally, it is conceivable that in addition to the water, the zinc source and the titanium-containing zeolitic material having framework type MWW, the aqueous suspension comprises one or more further suitable components. Preferably at least 99 weight-%, more preferably at least 99.5 weight-%, more preferably at least 99.9 weight-% of the aqueous suspension prepared in (ii) consist of water, the zinc source and the molding comprising the titanium-containing zeolitic material having framework type MWW.

It is conceivable that at least a portion of the water comprised in the aqueous suspension is ammonia-stabilized water.

Step (iii)

According to (iii), it is preferred that the aqueous suspension prepared in (ii) is heated to and kept at a temperature of the liquid phase of the aqueous suspension in the range of from 100 to 190° C., more preferably in the range of from 110 to 175° C., more preferably in the range of from 115 to 160° C., more preferably in the range of from 120 to 150° C. Preferred ranges are, for example, of from 120 to 130° C. or from 125 to 135° C. or from 130 to 140° C. or from 135 to 145° C. or from 140 to 150° C. Preferably, in (iii), the suspension prepared in (ii) is kept at this temperature for a period of time in the range of from 1 to 24 hours, more preferably in the range of from 2 to 17 hours, more preferably in the range of from 3 to 10 hours.

Preferably, during heating or during keeping or during heating and keeping in (iii), the suspension prepared in (ii) is not stirred.

Step (iv)

Generally, there are no specific restrictions how the separating in (iv) is carried out. Preferably, the separating in (iv) comprises subjecting the aqueous suspension obtained from (iii) to filtration or centrifugation, optionally followed by washing, obtaining the separated molding comprising zinc and a titanium-containing zeolitic material having framework type MWW. All types of filters are conceivable which preferably exhibit, during filtration, a loss of at most 10 weight-% in solid material. Conceivable filters include, for example, decantors, slot sieves, nutsch-type filters, and the like.

Step (v)

Preferably, the molding separated according to (iv) is subjected to drying according to (v). Prior to drying, it is conceivable to subject the molding separated according to (iv) to pre-drying in a suitable gas atmosphere such as nitrogen, air or lean air at a temperature of the gas atmosphere preferably of at most 50° C., more preferably of at most 40° C., more preferably of at most ° C., more preferably in the range of from 10 to 30° C., more preferably in the range of from 20 to 30° C.

Preferably, the separated molding comprising zinc and a titanium-containing zeolitic material having framework type MWW obtained from (iv) is dried at a temperature in the range of from 80 to 200° C., more preferably in the range of from 90 to 175° C., more preferably in the range of from 100 to 150° C. Preferably, in (v), the molding is dried at this temperature for a period of time in the range of from 0.5 to 12 hours, more preferably in the range of from 1 to 8 hours, more preferably in the range of from 2 to 6 hours. Preferably, the separated molding comprising zinc and a titanium-containing zeolitic material having framework type MWW is dried in a gas atmosphere comprising oxygen, preferably air or lean air, more preferably air, wherein the drying temperature mentioned above is the temperature of the gas atmosphere used for drying.

Step (vi)

Preferably, the molding separated according to (iv) or the molding obtained from drying according to (v), preferably the molding obtained from drying according to (v), is subjected to calcining according to (vi).

Preferably, the preferably dried molding comprising zinc and a titanium-containing zeolitic material having framework type MWW is calcined at a temperature in the range of from 300 to 600° C., preferably in the range of from 350 to 550° C., more preferably in the range of from 400 to 500° C. If calcination is carried out in a batch process, it may be preferred to carry out the calcining for a period of time in the range of from 0.1 to 6 hours, more preferably in the range of from 0.2 to 4 hours, more preferably in the range of from 0.5 to 3 hours. The calcining can also be carried out in a continuous process using, for example, a rotary furnace, a band calciner, or the like. Preferably, the preferably dried molding comprising zinc and a titanium-containing zeolitic material having framework type MWW is calcined in a gas atmosphere comprising oxygen, preferably air or lean air, more preferably air, wherein the calcining temperature mentioned above is the temperature of the gas atmosphere used for calcining.

According to the present invention, it is preferred that during the entire process, the molding is not subjected to water-steaming, more preferably not subjected to steaming.

Molding and Use Thereof

Further, the present invention relates to a molding comprising zinc and a titanium-containing zeolitic material having framework type MWW, obtainable or obtained by a process as described hereinabove, preferably according to a process as described hereinabove comprising drying according to (v), more preferably according to process comprising calcining according to (vi), more preferably comprising drying according to (v) and calcining according to (vi).

Further, the present invention relates to a molding comprising zinc and a titanium-containing zeolitic material having framework type MWW, wherein in the molding, the weight ratio of zinc relative to the titanium-containing zeolitic material having framework type MWW is in the range of from 0.005:1 to 0.1:1, preferably in the range of from 0.01:1 to 0.075:1, more preferably in the range of from 0.02:1 to 0.05:1, more preferably in the range of from 0.03:1 to 0.04:1.

Preferably, at least 99 weight-%, more preferably at least 99.5 weight-% of the molding consist of zinc, Ti, Si, O, and H. Preferably, the molding essentially consists of zinc, Ti, Si, O, and H. The term "essentially consists of" as used in this context of the present invention relates to a molding which, apart from any impurities which cannot be avoided in a given process for the preparation of the molding, the molding consists of zinc, Ti, Si, O, and H.

Preferably, the molding has a BET specific surface are of at least 200 to $m^2/g$, more preferably of at least 225 $m^2/g$, more preferably of at least 250 $m^2/g$, wherein the BET specific surface area is determined as described in Reference Example 1 herein.

Preferably, the molding has a crystallinity of at least 50%, preferably in the range of from 50 to 90%, wherein the crystallinity is determined as described in Reference Example 4 herein.

Preferably, the molding has a porosity of at least 0.9 mL/g, determined as described in Reference Example 2 herein.

Preferably, the molding has a mechanical strength in the range of from 9 to 23 N, preferably in the range of from 11 to 18 N, more preferably in the range of from 15 to 18 N, determined as described in Reference Example 3 herein.

Preferably, the molding exhibits a water adsorption capacity in the range of from 5 to 14 weight-%, preferably in the range of from 6 to 13 weight-%, more preferably in the range of from 8 to 12 weight-%, determined as described in Reference Example 7 herein.

Preferably, the molding exhibits a PO test parameter of at least 8%, preferably of at least 9%, determined as described in Reference Example 6 herein.

The molding of the present invention can be used for any conceivable purpose, including, but not limited to, an absorbent, an adsorbent, a molecular sieve, a catalyst, a catalyst carrier or an intermediate for preparing one or more thereof. Preferably, the molding is used as a catalyst, more preferably as a catalyst for converting a hydrocarbon, more preferably for oxidizing a hydrocarbon, more preferably for epoxidizing a hydrocarbon having at least one carbon-carbon double bond, more preferably for epoxidizing an alkene. Preferred alkenes include, bur are not limited to, ethene, propene, 1-butene, 2-butene, 1-pentene and 2-pentene. Propene is more preferred. Therefore, the present invention preferably relates to the use of the molding as a catalyst for epoxidizing propene. Preferably, the alkene, more preferably the propene, is epoxidized in the presence of a solvent, wherein the solvent preferably comprising a nitrile, more preferably comprises acetonitrile. More preferably, the solvent is acetonitrile, optionally in combination with water. Epoxidizing can be carried out using any conceivable epoxidation agent including the preferred hydrogen peroxide which can be used as such or can be formed in situ in the respective epoxidation reaction.

Further, the present invention relates to a method for catalytically converting a hydrocarbon, preferably for catalytically oxidizing a hydrocarbon, more preferably for catalytically epoxidizing a hydrocarbon having at least one carbon-carbon double bond, more preferably for catalytically epoxidizing an alkene, wherein the hydrocarbon, preferably the hydrocarbon having at least one carbon-carbon double bond, more preferably the alkene is brought into contact with the molding according to the present invention. Preferred alkenes include, bur are not limited to, ethene, propene, 1-butene, 2-butene, 1-pentene and 2-pentene. Propene is more preferred. Preferably, the alkene, more preferably the propene, is epoxidized in the presence of a solvent, wherein the solvent preferably comprising a nitrile, more preferably comprises acetonitrile. More preferably, the solvent is acetonitrile, optionally in combination with water. Epoxidizing can be carried out using any conceivable epoxidation agent including the preferred hydrogen peroxide which can be used as such or can be formed in situ in the respective epoxidation reaction.

Yet further, the present invention relates to a catalytic system comprising a catalyst comprising a molding according to any one of embodiments 52 to 60, and at least one potassium salt, wherein the at least one potassium salt is selected from the group consisting of at least one inorganic potassium salt, at least one organic potassium salt, and combinations of at least one inorganic potassium salt and at least one organic potassium salt. The at least one potassium salt is preferably selected from the group consisting of at least one inorganic potassium salt selected from the group consisting of potassium hydroxide, potassium chloride, potassium nitrate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts. Preferably, said catalytic system is a catalytic system for the epoxidation of an alkene, preferably propene. Preferably, said catalytic system is obtainable or obtained by a preferably continuous process comprising (i') providing a liquid feed stream comprising an alkene, preferably propene, hydrogen peroxide, a solvent, preferably, acetonitrile, water, the at least one, dissolved, potassium salt;

(ii') passing the liquid feed stream provided in (i') into an epoxidation reactor comprising the catalyst comprising a molding according to the present invention;

wherein in (i'), the molar ratio of potassium relative to hydrogen peroxide in the liquid feed stream is preferably in the range of from $5 \times 10^{-6}:1$ to $1000 \times 10^{-6}:1$, preferably from $25 \times 10^{-6}:1$ to $500 \times 10^{-6}:1$, more preferably from $50 \times 10^{-6}:1$ to $250 \times 10^{-6}:1$;

wherein the process preferably comprises (iii') subjecting the liquid feed stream to epoxidation reaction conditions in the epoxidation reactor, obtaining a reaction mixture comprising an alkene oxide, preferably propylene oxide, solvent, preferably acetonitrile, water, the at least one potassium salt, and optionally non-epoxidized alkene, preferably non-epoxidized propene.

Yet further, the present invention relates to a process for preparing an alkene oxide, preferably propylene oxide, said process comprising (i') providing a liquid feed stream comprising an alkene, preferably propene, hydrogen peroxide, a solvent, preferably, acetonitrile, water, the at least one, dissolved, potassium salt;

(ii') passing the liquid feed stream provided in (i') into an epoxidation reactor comprising the catalyst comprising a molding according to the present invention;

(iii') subjecting the liquid feed stream to epoxidation reaction conditions in the epoxidation reactor, obtaining a reaction mixture comprising an alkene oxide, preferably propylene oxide, solvent, preferably acetonitrile, water, the at least one potassium salt, and optionally non-epoxidized alkene, preferably non-epoxidized propene;

wherein in (i'), the molar ratio of potassium relative to hydrogen peroxide in the liquid feed stream is preferably in the range of from $5 \times 10^{-6}:1$ to $1000 \times 10^{-6}:1$, preferably from $25 \times 10^{-6}:1$ to $500 \times 10^{-6}:1$, more preferably from $50 \times 10^{-6}:1$ to $250 \times 10^{-6}:1$.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4".

1. A process for preparing a molding comprising zinc and a titanium-containing zeolitic material having framework type MWW, comprising
   (i) providing a molding comprising a titanium-containing zeolitic material having framework type MWW;
   (ii) preparing an aqueous suspension comprising a zinc source and the molding comprising a titanium-containing zeolitic material having framework type MWW prepared in (i);
   (iii) heating the aqueous suspension prepared in (ii) under autogenous pressure to a temperature of the liquid phase of the aqueous suspension in the range of from 100 to 200° C., obtaining an aqueous suspension comprising a molding comprising zinc and a titanium-containing zeolitic material having framework type MWW;
   (iv) separating the molding comprising zinc and a titanium-containing zeolitic material having framework type MWW from the liquid phase of the suspension obtained in (iii).

2. The process of embodiment 1, wherein the molding provided in (i) comprises the titanium-containing zeolitic material having framework type MWW and a binder.

3. The process of embodiment 2, wherein at least 90 weight-%, preferably at least 95 weight-%, more preferably at least 99 weight-%, more preferably at least 99.9 weight-% of the molding provided in (i) consist of the titanium-containing zeolitic material having framework type MWW and the binder.

4. The process of embodiment 2 or 3, wherein in the molding provided in (i), the weight ratio of the titanium-containing zeolitic material having framework type MWW relative to the binder is in the range of from 1:1 to 9:1, preferably in the range of from 2:1 to 7:1, more preferably in the range of from 3:1 to 5:1, wherein the binder is preferably a silica binder.

5. The process of any one of embodiments 1 to 4, wherein the molding provided in (i) is in the form of a tablet, a sphere, a cylinder, a star, a strand, or a trilob, wherein the molding is preferably a strand, more preferably an extrudate strand, preferably having rectangular, triangular hexagonal, quadratic, oval, or circular cross-section, wherein the diameter of the preferred circular cross-section is preferably in the range of from 1.0 to 2.0 mm.

6. The process of any one of embodiments 1 to 5, wherein the molding provided in (i) exhibits one or more of the following characteristics (1) to (3), preferably two or more of the following characteristics (1) to (3), more preferably the following characteristics (1) to (3):
   (1) a BET specific surface area of at least 300 m²/g determined as described in Reference Example 1 herein;
   (2) a pore volume of at least 0.9 mL/g, determined as described in Reference Example 2 herein;
   (3) a mechanical strength in the range of from 5 to 10 N, preferably in the range of from 6 to 9 N, determined as described in Reference Example 3 herein.

7. The process of any one of embodiments 1 to 6, preferably of any one of embodiments 2 to 6, wherein the molding comprising the titanium-containing zeolitic material having framework type MWW provided in (i) is obtainable or obtained by a process comprising
   (i.1) preparing a mixture comprising the titanium-containing zeolitic material having framework type MWW, a binder or a source of a binder, a pasting agent and optionally a pore-forming agent;
   (i.2) shaping the mixture prepared in (i.1), obtaining a molding comprising the titanium-containing zeolitic material having framework type MWW and a binder or a source of a binder:
   (i.3) drying the molding obtained in (i.2);
   (i.4) calcining the dried molding obtained in (i.3), obtaining the molding comprising the titanium-containing zeolitic material having framework type MWW and a binder.

8. The process of any one of embodiments 1 to 6, preferably of any one of embodiments 2 to 6, wherein providing the molding according to (i) comprises
   (i.1) preparing a mixture comprising the titanium-containing zeolitic material having framework type MWW, a binder or a source of a binder, and a pasting agent;
   (i.2) shaping the mixture prepared in (i.1), obtaining a molding comprising the titanium-containing zeolitic material having framework type MWW and a binder or a source of a binder:
   (i.3) drying the molding obtained in (i.2);
   (i.4) calcining the dried molding obtained in (i.3), obtaining the molding comprising the titanium-containing zeolitic material having framework type MWW and a binder.

9. The process of embodiment 7 or 8, wherein the pasting agent according to (i.1) comprises one or more of water and a carbohydrate, preferably water and a carbohydrate.

10. The process of any one of embodiments 7 to 9, wherein the mixture prepared in (i.1) comprises a pore-forming agent, preferably a mesopore-forming agent, which is preferably one or more a polyalkylene oxide such as polyethylene oxide, a polystyrene, a polyacrylate, a polymethacrylate, a polyolefin, a polyamide, and a polyester.

11. The process of any one of embodiments 7 to 10, wherein the mixture prepared in (i.1) does not comprise a mesopore-forming agent, preferably does not comprise a pore-forming agent, which is preferably one or more of a polyalkylene oxide such as polyethylene oxide, a polystyrene, a polyacrylate, a polymethacrylate, a polyolefin, a polyamide, and a polyester.
12. The process of any one of embodiments 7 to 11, wherein the binder or precursor of a binder is a silica binder or a precursor of a silica binder, wherein more preferably, the silica binder or the precursor comprises, preferably is, colloidal silica.
13. The process of any one of embodiments 7 to 12, wherein in the mixture prepared in (i.1), the weight ratio of the titanium-containing zeolitic material having framework type MWW relative to the silica comprised in the binder or the precursor of the binder is in the range of from 1:1 to 9:1, preferably in the range of from 2:1 to 7:1, more preferably in the range of from 3:1 to 5:1.
14. The process of any one of embodiments 7 to 13, wherein the mixture prepared in (i.1) does not comprise zinc.
15. The process of any one of embodiments 7 to 14, wherein at least 99 weight-%, preferably at least 99.5 weight-%, more preferably at least 99.9 weight-% of the mixture prepared in (i.1) consist of the titanium-containing zeolitic material having framework type MWW, the binder or the precursor of the binder, and the pasting agent.
16. The process of any one of embodiments 7 to 15, wherein preparing the mixture according to (i.1) comprises kneading the mixture.
17. The process of any one of embodiments 7 to 16, wherein shaping according to (i.2) comprises extruding the mixture prepared in (i.1).
18. The process of embodiment 17, wherein from extruding, a molding is obtained in the form of a strand, preferably having a diameter in the range of from 1.0 to 2.0 mm.
19. The process of any one of embodiments 7 to 18, wherein according to (i.3), the molding is dried at a temperature in the range of from 80 to 200° C., preferably in the range of from 90 to 175° C., more preferably in the range of from 100 to 150° C.
20. The process of any one of embodiments 7 to 19, wherein according to (i.3), the molding is dried in a gas atmosphere comprising oxygen, preferably in air or lean air, more preferably in air.
21. The process of any one of embodiments 7 to 20, wherein according to (i.4), the molding is calcined at a temperature in the range of from 350 to 650° C., preferably in the range of from 400 to 600° C., more preferably in the range of from 450 to 550° C.
22. The process of any one of embodiments 7 to 21, wherein according to (i.4), the molding is calcined in a gas atmosphere comprising oxygen, preferably in air or lean air, more preferably in air.
23. The process of any one of embodiments 1 to 22, wherein at least 99 weight-% of the titanium-containing zeolitic material having framework type MWW comprised in the molding provided in (i) consist of Ti, Si, O, and H.
24. The process of any one of embodiments 1 to 23, wherein the titanium-containing zeolitic material having framework type MWW comprised in the molding provided in (i) has a titanium content, calculated as elemental titanium, in the range of from 0.1 to 5 weight-%, preferably in the range of from 0.5 to 3 weight-%, more preferably in the range of from 1 to 3 weight-%, based on the total weight of the titanium-containing zeolitic material having framework type MWW.
25. The process of any one of embodiments 1 to 24, wherein the titanium-containing zeolitic material having framework type MWW comprised in the molding provided in (i) has a silicon content, calculated as elemental silicon, in the range of from 30 to 60 weight-%, preferably in the range of from 35 to 55 weight-%, more preferably in the range of from 40 to 50 weight-%, more preferably in the range of from 1 to 3 weight-%, based on the total weight of the titanium-containing zeolitic material having framework type MWW.
26. The process of any one of embodiments 1 to 25, wherein the titanium-containing zeolitic material having framework type MWW comprised in the molding provided in (i) has a total organic carbon content of at most 0.1 weight-%, based on the total weight of the titanium-containing zeolitic material having framework type MWW.
27. The process of any one of embodiments 1 to 26, wherein the titanium-containing zeolitic material having framework type MWW comprised in the molding provided in (i) has a boron content, calculate as elemental boron, of at most 0.5 weight-%, based on the total weight of the titanium-containing zeolitic material having framework type MWW.
28. The process of any one of embodiments 1 to 27, wherein the titanium-containing zeolitic material having framework type MWW comprised in the molding provided in (i) has a BET specific surface area of at least 400 m$^2$/g, preferably in the range of from 400 to 600 m$^2$/g, more preferably in the range of from 450 to 550 m$^2$/g, wherein the BET specific surface area is determined as described in Reference Example 1 herein.
29. The process of any one of embodiments 1 to 28, wherein the titanium-containing zeolitic material having framework type MWW comprised in the molding provided in (i) has a crystallinity of at least 70%, preferably in the range of from 70 to 90%, more preferably in the range of from 70 to 80%, wherein the crystallinity is determined as described in Reference Example 4 herein.
31. The process of any one of embodiments 1 to 30, wherein the titanium-containing zeolitic material having framework type MWW comprised in the molding provided in (i) is in the form of a powder having a particle size distribution characterized by a Dv10 value in the range of from 1 to 10 micrometer, preferably in the range of from 1.5 to 10 micrometer, more preferably in the range of from 2 to 6 micrometer, a Dv50 value in the range of from 5 to 50 micrometer, preferably in the range of from 7 to 50 micrometer, more preferably in the range of from 8 to 30 micrometer, and a Dv90 value in the range of from 12 to 200 micrometer, preferably in the range of from 12 to 90 micrometer, more preferably in the range of from 13 to 70 micrometer, wherein the particle size distribution is determined as described in Reference Example 5 herein.
32. The process of any one of embodiments 1 to 31, wherein the titanium-containing zeolitic material having framework type MWW comprised in the molding provided in (i) is a spray powder.
33. The process of any one of embodiments 1 to 32, wherein in (ii), the zinc source comprises a zinc compound which is soluble in water at the temperature and pressure of the liquid aqueous phase according to (iii).
34. The process of any one of embodiments 1 to 33, wherein in (ii), the zinc source comprises one or more of a zinc salt soluble in water preferably being a zinc salt of an organic or inorganic acid, preferably comprises one or more of zinc acetate, zinc benzoate, zinc borate, zinc bromide, zinc chloride, zinc formate, zinc gluconate, zinc lactate, zinc laurate, zinc malate, zinc nitrate, zinc perborate, zinc sulfate, zinc sulfamate, zinc tartrate, more preferably comprises zinc acetate, more preferably comprises zinc acetate dihydrate.

35. The process of any one of embodiments 1 to 34, wherein in (ii), the zinc source comprises zinc acetate, preferably comprises zinc acetate dihydrate, more preferably is zinc acetate dihydrate.

36. The process of any one of embodiments 1 to 35, wherein in the aqueous suspension prepared in (ii), the weight ratio of zinc comprised in the zinc source relative to the titanium-containing zeolitic material having framework type MWW comprised in the molding is in the range of from 0.005:1 to 0.1:1, preferably in the range of from 0.01:1 to 0.075:1, more preferably in the range of from 0.02:1 to 0.05:1, more preferably in the range of from 0.03:1 to 0.04:1.

37. The process of any one of embodiments 1 to 36, wherein in the aqueous suspension prepared in (ii), the weight ratio of the titanium-containing zeolitic material having framework type MWW comprised in the molding relative to water is in the range of from 0.01:1 to 0.1:1, preferably in the range of from 0.02:1 to 0.075:1, more preferably in the range of from 0.03:1 to 0.05:1.

38. The process of any one of embodiments 1 to 37, wherein at least 99 weight-%, preferably at least 99.5 weight-%, more preferably at least 99.9 weight-% of the aqueous suspension prepared in (ii) consist of water, the zinc source and the molding comprising the titanium-containing zeolitic material having framework type MWW.

39. The process of any one of embodiments 1 to 38, wherein in (iii), the suspension prepared in (ii) is heated to and kept at a temperature of the liquid phase of the aqueous suspension in the range of from 110 to 175° C., preferably in the range of from 120 to 150° C.

40. The process of any one of embodiments 1 to 39, wherein in (iii), the suspension prepared in (ii) is kept at the temperature for a period of time in the range of from 1 to 24 hours, preferably in the range of from 2 to 17 hours, more preferably in the range of from 3 to 10 hours.

41. The process of any one of embodiments 1 to 40, wherein during heating and keeping in (iii), the suspension prepared in (ii) is not stirred.

42. The process of any one of embodiments 1 to 41, wherein in (iv), the separating comprises subjecting the aqueous suspension obtained from (iii) to filtration or centrifugation, optionally followed by washing, obtaining the separated molding comprising zinc and a titanium-containing zeolitic material having framework type MWW.

43. The process of any one of embodiments 1 to 42, further comprising
   (v) drying the separated molding comprising zinc and a titanium-containing zeolitic material having framework type MWW obtained from (iv).

44. The process of embodiment 43, wherein the separated molding comprising zinc and a titanium-containing zeolitic material having framework type MWW is dried at a temperature in the range of from 80 to 200° C., preferably in the range of from 90 to 175° C., more preferably in the range of from 100 to 150° C.

45. The process of embodiment 43 or 44, wherein the separated molding comprising zinc and a titanium-containing zeolitic material having framework type MWW is dried for a period of time in the range of from 0.5 to 12 hours, preferably in the range of from 1 to 8 hours, more preferably in the range of from 2 to 6 hours.

46. The process of any one of embodiments 43 to 45, wherein the separated molding comprising zinc and a titanium-containing zeolitic material having framework type MWW is dried in a gas atmosphere comprising oxygen, preferably air or lean air, more preferably air.

47. The process of any one of embodiments 43 to 46, further comprising
   (vi) calcining the dried molding comprising zinc and a titanium-containing zeolitic material having framework type MWW obtained from (v).

48. The process of embodiment 47, wherein the dried molding comprising zinc and a titanium-containing zeolitic material having framework type MWW is calcined at a temperature in the range of from 300 to 600° C., preferably in the range of from 350 to 550° C., more preferably in the range of from 400 to 500° C.

49. The process of embodiment 47 or 48, wherein the dried molding comprising zinc and a titanium-containing zeolitic material having framework type MWW is calcined for a period of time in the range of from 0.1 to 6 hours, preferably in the range of from 0.2 to 4 hours, more preferably in the range of from 0.5 to 3 hours.

50. The process of any one of embodiments 47 to 49, wherein the dried molding comprising zinc and a titanium-containing zeolitic material having framework type MWW is calcined in a gas atmosphere comprising oxygen, preferably air or lean air, more preferably air.

51. The process of any one of embodiments 1 to 50, wherein the molding comprising zinc and a titanium-containing zeolitic material having framework type MWW is not subjected to water-steaming, preferably is not subjected to steaming.

52. A molding comprising zinc and a titanium-containing zeolitic material having framework type MWW, obtainable or obtained or preparable or prepared by a process according to any one of embodiments 1 to 51, preferably according to any one of embodiments 33 to 51, more preferably according to any one of embodiments 43 to 51, more preferably according to any one of embodiments 47 to 51.

53. A molding comprising zinc and a titanium-containing zeolitic material having framework type MWW, preferably the molding according to embodiment 52, wherein in the molding, the weight ratio of zinc relative to the titanium-containing zeolitic material having framework type MWW is in the range of from 0.005:1 to 0.1:1, preferably in the range of from 0.01:1 to 0.075:1, more preferably in the range of from 0.02:1 to 0.05:1, more preferably in the range of from 0.03:1 to 0.04:1.

54. The molding of embodiment 53, wherein at least 99 weight-%, preferably at least 99.5 weight-% of the molding consist of zinc, Ti, Si, 0, and H.

55. The molding of embodiment 53 to 54, having a BET specific surface are of at least 200 to m²/g, preferably of at least 250 m²/g, wherein the BET specific surface area is determined as described in Reference Example 1 herein.

56. The molding of any one of embodiments 53 to 55, having a crystallinity of at least 50%, preferably in the range of from 50 to 90%, wherein the crystallinity is determined as described in Reference Example 4 herein.

57. The molding of any one of embodiments 53 to 56, having a porosity of at least 0.9 mL/g, determined as described in Reference Example 2 herein.

58. The molding of any one of embodiments 53 to 57, having a mechanical strength in the range of from 9 to 23 N, preferably in the range of from 11 to 18 N, more preferably in the range of from 15 to 18 N, determined as described in Reference Example 3 herein.

59. The molding of any one of embodiments 53 to 57, exhibiting a water adsorption capacity in the range of from 5 to 14 weight-%, preferably in the range of from 6 to 13 weight-%, more preferably in the range of from 8 to 12 weight-%, determined as described in Reference Example 7 herein.
60. The molding of any one of embodiments 53 to 59, exhibiting a PO test parameter of at least 8%, preferably of at least 9%, determined as described in Reference Example 6 herein.
61. Use of a molding according to any one of embodiments 52 to 60 as a catalyst for converting a hydrocarbon, preferably as a catalyst for oxidizing a hydrocarbon, more preferably for epoxidizing a hydrocarbon having at least one carbon-carbon double bond, more preferably for epoxidizing an alkene.
62. The use of embodiment 61 for epoxidizing one or more of propene, ethene, 1-butene, 2-butene, 1-pentene and 2-pentene, preferably for epoxidizing propene.
63. The use of embodiment 61 or 62, wherein the alkene, preferably propene, is epoxidized in the presence of a solvent preferably comprising a nitrile, more preferably acetonitrile.
64. The use of embodiment 62 or 63, wherein the propene is epoxidized with hydrogen peroxide as epoxidizing agent.
65. A method for catalytically converting a hydrocarbon, preferably for catalytically oxidizing a hydrocarbon, more preferably for catalytically epoxidizing a hydrocarbon having at least one carbon-carbon double bond, more preferably for catalytically epoxidizing an alkene, wherein the hydrocarbon, preferably the hydrocarbon having at least one carbon-carbon double bond, more preferably the alkene is brought into contact with the molding according to any one of embodiments 52 to 60 as catalyst.
66. The method of embodiment 65 for catalytically epoxidizing one or more of propene, ethene, 1-butene, 2-butene, 1-pentene and 2-pentene, preferably for catalytically epoxidizing propene.
67. The method of embodiment 66, wherein the alkene, preferably propene, is epoxidized in the presence of a solvent preferably comprising a nitrile, more preferably acetonitrile.
68. The method of embodiment 66 or 67, wherein the propene is epoxidized with hydrogen peroxide as epoxidizing agent.
69. A catalytic system comprising a catalyst comprising a molding according to any one of embodiments 52 to 60, and at least one potassium salt, wherein the at least one potassium salt is selected from the group consisting of at least one inorganic potassium salt, at least one organic potassium salt, and combinations of at least one inorganic potassium salt and at least one organic potassium salt.
70. The catalytic system of embodiment 69, wherein the at least one potassium salt is selected from the group consisting of at least one inorganic potassium salt selected from the group consisting of potassium hydroxide, potassium chloride, potassium nitrate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts.
71. The catalytic system of embodiment 69 or 70 for the epoxidation of an alkene, preferably propene.
72. The catalytic system of any one of embodiments 69 to 71, obtainable or obtained by a preferably continuous process comprising
    (i') providing a liquid feed stream comprising an alkene, preferably propene, hydrogen peroxide, a solvent, preferably, acetonitrile, water, the at least one, dissolved, potassium salt;
    (ii') passing the liquid feed stream provided in (i') into an epoxidation reactor comprising a catalyst comprising a molding according to any one of embodiments 52 to 60;
    wherein in (i'), the molar ratio of potassium relative to hydrogen peroxide in the liquid feed stream is preferably in the range of from $5 \times 10^{-6}:1$ to $1000 \times 10^{-6}:1$, preferably from $25 \times 10^{-6}:1$ to $500 \times 10^{-6}:1$, more preferably from $50 \times 10^{-6}:1$ to $250 \times 10^{-6}:1$;
    wherein the process preferably comprises
    (iii') subjecting the liquid feed stream to epoxidation reaction conditions in the epoxidation reactor, obtaining a reaction mixture comprising an alkene oxide, preferably propylene oxide, solvent, preferably acetonitrile, water, at least a portion of the dissolved potassium salt, and optionally non-epoxidized alkene, preferably non-epoxidized propene.
73. A preferably continuous process for preparing an alkene oxide, preferably propylene oxide, said process comprising
    (i') providing a liquid feed stream comprising an alkene, preferably propene, hydrogen peroxide, a solvent, preferably, acetonitrile, water, and preferably a dissolved potassium salt;
    (ii') passing the liquid feed stream provided in (i') into an epoxidation reactor comprising a catalyst comprising a molding according to any one of embodiments 52 to 60;
    (iii') subjecting the liquid feed stream to epoxidation reaction conditions in the epoxidation reactor, obtaining a reaction mixture comprising an alkene oxide, preferably propylene oxide, solvent, preferably acetonitrile, water, at least a portion of the dissolved potassium salt, and optionally non-epoxidized alkene, preferably non-epoxidized propene;
    wherein in (i'), the molar ratio of potassium relative to hydrogen peroxide in the liquid feed stream is preferably in the range of from $5 \times 10^{-6}:1$ to $1000 \times 10^{-6}:1$, preferably from $25 \times 10^{-6}:1$ to $500 \times 10^{-6}:1$, more preferably from $50 \times 10^{-6}:1$ to $250 \times 10^{-6}$.

The present invention is further illustrated by the following reference examples, examples and comparative examples.

EXAMPLES

Reference Example 1: Determination of BET Specific Surface Area

The BET specific surface area (multipoint BET specific surface area) referred to in the context of the present application was determined via nitrogen adsorption at 77 K as described in DIN 66131.

Reference Example 2: Determination of Hg Porosimetry Data

The porosimetry data via Hg porosimetry were determined as described in DIN 66133.

Reference Example 3: Determination of Mechanical Strength

The mechanical strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS15", version 1.5, December 2001 by Zwick GmbH & Co. Technische Dokumentation, August-Nagel-Strasse 11, D-89079 Ulm, Germany. With said machine, a given strand according to the present invention, described in the examples herein, is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 4: Determination of the Crystallinity

The crystallinity referred to in the context of the present application was determined according to the method as described in the User Manual DIFFRAC.EVA Version 3, page 105, from Bruker AXS GmbH, Karlsruhe (published February 2003). The respective data were collected on a standard Bruker D8 Advance Diffractometer Series II using a LYNXEYE detector, from 2° to 50° 2 theta, using fixed slits, a step size of 0.02° 2 theta and a scan speed of 2.4 s/step. The parameters used for estimating the background/amorphous content were Curvature=0 and Threshold=0.8.

Reference Example 5: Determination of the Particle Size Distribution

The particle size distribution, referred to in the context of the present application on the basis of the respective Dv10, Dv50 and Dv90 values, was determined according to the following method: 1.0 g of a given material was suspended in 100 g deionized water and stirred for 1 min. The particle size distribution was then determined using a Mastersizer S long bed version 2.15, ser. No. 33544-325; supplier: Malvern Instruments GmbH, Herrenberg, Germany, with the following parameters:
 focal width: 300RF mm
 beam length: 10.00 mm
 module: MS17
 shadowing: 16.9%
 dispersion model: 3$$D
 analysis model: polydisperse
 correction: none The term "Dv10 value" as referred to in the context of the present invention describes the average particle size where 10 volume-% of the particles of the micropowder have a smaller size. Similarly, the term "Dv50 value" as referred to in the context of the present invention describes the average particle size where 50 volume-% of the particles of the micropowder have a smaller size, and the term "Dv90 value" as referred to in the context of the present invention describes the average particle size where 90 volume-% of the particles of the micropowder have a smaller size.

Reference Example 6: PO Test

In the PO test, the moldings of the present invention are tested as catalysts in a mini autoclave by reaction of propene with an aqueous hydrogen peroxide solution (30 weight-%) to yield propylene oxide. In particular, 0.63 g of the moldings of the invention were introduced together with 79.2 g of acetonitrile and 12.4 g of propene at room temperature, and 22.1 g of hydrogen peroxide (30 weight-% in water) were introduced in a steel autoclave. After a reaction time of 4 hours at 40° C., the mixture was cooled and depressurized, and the liquid phase was analyzed by gas chromatography with respect to its propylene oxide content. The propylene oxide content of the liquid phase (in weight-%) is the result of the PO test.

The PO test rate was determined following the pressure progression during the PO test described above. The pressure progression was recorded using a S-11 transmitter (from Wika Alexander Wiegand SE & Co. KG), which was positioned in the pressure line of the autoclave, and a graphic plotter Buddeberg 6100A. The respectively obtained data were read out and depicted in a pressure progression curve. The pressure drop rate, i.e. the PO test rate, was determined according to the following equation:

$$PDR=[p(\max)-p(\min)]/\text{delta } t$$

wherein
PDR/(bar/min)=pressure drop rate
p(max)/bar=maximum pressure at the start of the reaction
p(min)/bar=minimum pressure observed during the reaction
delta t/min=time difference from the start of the reaction to the point in time where p(min) was observed Reference Example 7: Determination of Water Adsorption The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 wt. %). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 wt. % from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 wt. % to 5 wt. % with a step of 10% and the change in the weight of the sample (water uptake) was monitored and recorded.

Reference Example 8: Preparation of a Titanium-Containing Zeolitic Material Having Framework Type MWW A titanium-containing zeolite (spray powder) was prepared as described in Example 5, 5.1 to 5.3, of WO 2013/117536 A, page 83, line 26 to page 92, line 7.

Reference Example 9: Continuous Epoxidation Reaction

Continuous epoxidation reaction was carried out as described in WO 2015/010990 A, in Reference Example 1, page 55, line 14 to page 57, line 10. The reaction temperature was set to a value of 45° C. (see WO 2015/010990 A, page 56, lines 16 to 18). The temperature was adjusted to achieve an essentially constant hydrogen peroxide conversion of 90% (see WO 2015/010990 A, page 56, lines 21 to 23). $KH_2PO_4$ was employed as additive (see WO 2015/010990 A, page 56, lines 7 to 10), the concentration of the additive was 130 micromol per mol hydrogen peroxide. As catalysts, the catalysts according to Comparative Example 1 and Example 1 hereinbelow were employed (see WO 2015/010990 A, page 55, lines 16 to 18).

Reference examples 10 to 12 which follow herewith are examples of how to provide a titanium-containing zeolitic material having framework type MWW, having a water absorption capacity of at least 11 weight-%.

Reference Example 10: Providing a Titanium-Containing Zeolitic Material Having Framework Type MWW, Having a Water Absorption Capacity of at Least 11 Weight-%

(i) B—Ti-MWW Synthesis

The synthesis mixture had the following composition: 1.0 ($SiO_2$): 0.04 ($TiO_2$): 0.67 ($B_2O_3$): 1.4 piperidine: $19H_2O$.

Batch 0: 1,026 g of deionized water were initially introduced into a beaker, 365 g of piperidine were then added with stirring at 200 rpm, and the mixture was stirred for 10 min at pH 13.2 at about 23° C. Thereafter, the batch was divided into two equal parts.

Batch 1: 695.5 g of the deionized water-piperidine solution were placed in a beaker and, with stirring at 200 rpm, 248.4 g of boric acid were added and stirring was continued for 30 min, then 90 g of fumed silica (Cab-O-SIL® 5M) was added at about 23° C. The mixture was then stirred for 1 h at pH 11.4 at about 23° C.

Batch 2: 695.5 g of the deionized water-piperidine solution were initially introduced into a beaker, with stirring at 200 rpm at about 23° C., 43.2 g of tetrabutyl orthotitanate were added and stirring was continued for a further 30 minutes and then 90 g of fumed silica (Cab-O-SIL® 5M) were added. The mixture was then stirred for 1 h at pH 12.2 at about 23° C.

Batch 3: The two suspensions from batch 1 and 2 were mixed together for 1.5 h at pH 11.8 at about 23° C. to obtain the synthesis mixture and then crystallization was carried out in an autoclave under the following conditions:

Heating in 1 h to 130° C./keeping for 24 h at 100 rpm at a pressure of from 0-2.7 bar, then, heating in 1 h to 150° C./keeping for 24 h at 100 rpm at a pressure of from 2.7-4.9 bar, then, heating in 1 h to 170° C./keeping for 120 h at 100 rpm at a pressure of from 4.9-9.4 bar.

After the above crystallization conditions, the thus obtained suspension having a pH of 11.3 was drained and filtered through a suction filter (giving a clear filtrate) and washed with 10 liters of deionized water (giving a turbid filtrate). The turbid filtrate was then acidified to pH 7 with 10% aqueous $HNO_3$. Subsequently, the moist product (filter cake) was filled into a porcelain dish, dried overnight, then ground. The yield was 192.8 g. According to the elemental analysis the resulting product had the following contents determined per 100 g substance of 9.6 g carbon, 0.85 g B, 21.8 g Si and 17.8 g Ti.

(ii) B—Ti-MWW $HNO_3$ Treatment

The dried and ground material obtained according to item (i) above was washed with $HNO_3$ solution (ratio of solid to liquid 1 g:20 ml) for 20 h at 100° C.: In a 10 liter glass flask 3600 g $HNO_3$ solution and 180 g B—Ti-MWW according to item (i) were added at 100° C., followed by boiling for 20 hours at reflux with stirring at 250 rpm. The thus obtained white suspension was filtered off and washed with 2×5 liters of deionized water. Drying: 10 h/120° C. Calcination: heating at 2 K/min to 530° C./keeping for 5 h. The yield was 143 g. According to the elemental analysis the resulting product had the following contents determined per 100 g substance: <0.1 g carbon (TOC), 0.27 g B, 42 g Si, and 2 g Ti. The BET surface area was determined to be 532 m²/g. The crystallinity of the product was measured (Reference Example 8) to be 80% and the average crystal size as calculated from the XRD diffraction data was determined to be 22 nm.

(iii) B—Ti-MWW $HNO_3$ Treatment

The material obtained according to item (ii) above was washed with $HNO_3$ solution (ratio of solid to liquid 1 g:20 ml) for 20 h at 100° C. In a 10 liter glass flask, 2,400 g of $HNO_3$ solution and 120 g of B—Ti-MWW according to item (ii) were added at 100° C., followed by boiling for 20 hours at reflux with stirring at 250 rpm. The white suspension was filtered off and washed with 7×1 liter of deionized water. Drying: 10 h/120° C. Calcination: heating at 2 K/min to 530° C./keeping for 5 h. The yield was 117 g. According to the elemental analysis the resulting product had the following contents determined per 100 g substance: <0.03 g B, 44 g Si, and 1.8 g Ti. The BET specific surface area was determined to be 501 m²/g. The crystallinity of the product was measured to be 94% and the average crystal size as calculated from the XRD diffraction data was determined to be 22 nm. The XRD of the resulting product confirmed that the zeolitic material obtained had an MWW framework structure. The water adsorption capacity as determined by Reference Example 1 herein was 13.2 weight-%.

Reference Example 11: Providing a Titanium-Containing Zeolitic Material Having Framework Type MWW, Having a Water Absorption Capacity of at Least 11 Weight-%

(i) B—Ti-MWW Synthesis

The synthesis mixture had the following composition: 1.0 ($SiO_2$): 0.04 ($TiO_2$): 0.67 ($B_2O_3$): 1.4 piperidine: $19H_2O$.

Batch 0: 1,026 g of deionized water were initially introduced into a beaker, 365 g of piperidine were added with stirring at 200 rpm, and the mixture was stirred for 10 min at pH 13.2 at about 23° C. Thereafter, the batch was divided into two equal parts.

Batch 1: 695.5 g of deionized water-piperidine solution were placed in a beaker and, with stirring at 200 rpm, 248.4 g of boric acid were added and stirring was continued for 30 minutes, then 90 g of fumed silica (Cab-O-SIL® 5M) were added at about 23° C. The mixture was then further stirred for 1 h at pH 11.4 at about 23° C.

Batch 2: 695.5 g of deionized water-piperidine solution were initially introduced into a beaker, with stirring at 200 rpm at about 23° C., 43.2 g of tetrabutyl orthotitanate were added and stirring was continued for a further 30 min and then 90 g of fumed silica (Cab-O-SIL® 5M) were added. The mixture was then further stirred for 1 h at pH 12.2 at about 23° C.

Batch 3: The two suspensions from batch 1 and 2 were mixed together for 1.5 h at a pH of 11.8 at about 23° C. to obtain the synthesis mixture and then crystallization was carried out in an autoclave under the following conditions: heating in 1 h to 170° C./keeping for 120 h at 120 rpm at a pressure of from 0-9.4 bar. After the above crystallization conditions, the thus obtained suspension having a pH of 11.3 was drained and filtered through a suction filter and washed with 10 L of deionized water. Subsequently, the moist product (filter cake) was filled into a porcelain dish, dried overnight, then ground. The yield was 194 g.

(ii) B—Ti-MWW $HNO_3$ Treatment

The dried and ground material according to item (i) was then washed with $HNO_3$ solution (ratio of solid to liquid 1 g:20 ml) for 20 h at 100° C.: In a 10 liter glass flask 3,600 g aqueous $HNO_3$ solution and 180 g B—Ti-MWW according to item (i) were added at 100° C., followed by boiling for 20 h at reflux with stirring at 250 rpm. The thus obtained white suspension was filtered off and washed with 2×5 L of deionized water. Drying: 10 h/120° C. Calcination: heating at 2 K/min to 530° C./keeping for 5 h. The yield was 146 g. According to the elemental analysis the resulting product had the following contents determined per 100 g substance: <0.1 g carbon (TOC), 0.25 g B, 43 g Si and 2.6 g Ti. The BET specific surface area was determined to be 514 $m^2/g$. The crystallinity of the product was measured to be 79% and the average crystal size as calculated from the XRD diffraction data was determined to be 22.5 nm. The XRD of the resulting product confirmed that the zeolitic material obtained had an MWW framework structure. The water adsorption capacity as determined by Reference Example 1 herein was 17.3 weight-%.

Reference Example 12: Providing a Titanium-Containing Zeolitic Material Having Framework Type MWW, Having a Water Absorption Capacity of at Least 11 Weight-%

(i) B—Ti-MWW Synthesis

In order to prepare a synthesis mixture having the following composition: 1.0 $B_2O_3$/2.0 $SiO_2$/32.8 $H_2O$/2.43 piperidine, deionized water and boric acid were mixed together in a beaker at about 23° C., to which ammonium stabilized silica sol was added with further mixing at about 23° C. The thus obtained mixture was then transferred to an autoclave and piperidine was then added with further mixing. Crystallization was then carried out in the autoclave over 48 hours at 175° C. at autogenous pressure. Any excess piperidine was then flashed off. The resulting product was then filtered off as a solid, washed with deionized water and dried. Rotary calcination was then carried out at 650° C. for 2 hours.

(ii) Deboronation

A slurry of the thus obtained calcined product was then prepared with deionised water, such that the slurry had a solids content of 6.25 weight-%. The slurry was heated to 90.5° C. and then held at said temperature for 10 hours. The resulting (deboronated) product was then filtered off as a solid, washed with deionized water and dried.

(iii) Ti Insertion

A slurry was prepared with the deionized water and the deboronated product of item (ii) above, which was mixed at 23° C. Said slurry was then transferred to an autoclave, to which a tetra-n-butyl titanate/piperidine mixture was then added. The thus obtained mixture had the following composition: 0.035 $TiO_2$/1.0 $SiO_2$/17.0 $H_2O$/1.0 Piperidine. Crystallization was then carried out in the autoclave over 48 hours at 170° C. under autogenous pressure. Any excess piperidine/ethanol was then flashed off. The resulting product was then filtered off as a solid, washed with deionized water and dried.

(iv) Acid Treatment

A slurry was prepared from the product according to item (iii) in 10% $HNO_3$ (aqueous) solution (907.2 g $HNO_3$/453.6 g product of item (iii), thus a 5 weight-% solids slurry was produced. The slurry was heated to 93.3° C. and then held at said temperature for 1 hour. The resulting product was then filtered off as a solid, washed with deionized water and dried. Rotary calcination was then carried out at 650° C. for 2 hours. According to the elemental analysis the resulting calcinated product had the following contents determined per 100 g substance of 2 g carbon (TOC), 42 g Si and 1.6 g Ti. The BET specific surface area was determined to be 420 $m^2/g$. The crystallinity of the product was measured to be 82%. The XRD of the resulting product confirmed that the zeolitic material obtained had an MWW framework structure. The water adsorption capacity as determined by Reference Example 1 herein was 14.1 weight-%.

Comparative Example 1: Preparation of a Molding a Zinc- and Titanium-Containing Zeolitic Material Having Framework Type MWW Using the titanium-containing zeolite prepared according to Reference Example 8 above, a molding was prepared. In a first step CE1.1, the titanium-containing zeolite was impregnated with zinc so as to obtain a zinc- and titanium-containing zeolitic material having framework type MWW. In a second step CE1.2, the zinc- and titanium-containing zeolitic material having framework type MWW was subjected to shaping. The respectively obtained moldings were subjected to a water treatment in a third step CE1.3.

CE1.1: The titanium-containing zeolite prepared according to Reference Example 8 was subjected to zinc impregnation. The impregnation was carried out as described in WO 2013/117536 A, example 5.4, page 92, line 9 to page 94, line 8.

CE1.2: The shaping of the zinc- and titanium-containing zeolitic material having framework type MWW was carried out as described in WO 2013/117536 A, example 5.5, page 95, lines 10 to 36.

CE1.3: The water treatment of the moldings obtained from the second step was carried out as described in WO 2013/117536 A, example 5.6, page 97, lines 1 to 17.

Example 1: Preparation of a Molding Comprising Zinc and a Titanium-Containing Zeolitic Material Having Framework Type MWW Using the titanium-containing zeolite prepared according to Reference Example 8 above, a molding was prepared. In a first step E1.1, the titanium-containing zeolite was subjected to shaping. In a second step E1.2, the respectively obtained moldings were subjected to a water treatment wherein during said water treatment, zinc was incorporated into the moldings.

E1.1: 60 g of the titanium-containing zeolite prepared according to Reference Example 8 were admixed with 3 g of Walocel™ (5%; Wolf Walsrode AG) and 37.5 g Ludox® AS-40 (20 weight-% $SiO_2$ relative to zeolitic material) and kneaded for 10 min. Them 160 mL deionized water were added, and the resulting mixture was kneaded further. The total kneading time was 40 min. In a Loomis extruder, strands were prepared at a machine pressure of 54 bar from the kneaded mass, wherein said strands had a circular cross section with a diameter of 1.5 mm. In an oven, the strands were heated to a temperature of 120° C. at a heating rate of 3 K/min and dried at 120° C. for 4 h under air atmosphere. Then, the dried strands were heated to a temperature of 500° C. at a heating rate of 2 K/min and dried at 500° C. for 5 h under air atmosphere.

E1.2: 50 g of strands of the calcined strands obtained from E1.1 were added to 1,000 g of deionized water and 4.6 g zinc acetate dihydrate (Merck) in an autoclave without stirring. The mixture was heated to a temperature of 145° C. and kept at that temperature for 8 h under the autogenous pressure of 2.8 bar. The resulting strands were filtered off using a nutsch-type filter and washed five times with 200 mL of deionized water until the conductivity of the water obtained from the washing was below 30 microSiemens. In an oven, the respectively obtained strands were heated to a temperature of 120° C. within 60 min and dried at that temperature for 240 min under air atmosphere. Then, the dried strands were heated to a temperature of 450° C. within 165 min and calcined at that temperature for 120 min under air atmosphere.

Comparative Example 2: Preparation of a Molding a Zinc- and Titanium-Containing Zeolitic Material Having Framework Type MWW Example 1 was repeated, with the difference that in step E1.2 rather than autogeneous pressure, reflux conditions were employed.

More specifically, 50 g of strands of the calcined strands obtained from E1.1 were added to 1,000 g of deionized water and 4.6 g zinc acetate dihydrate (Merck), which was then heated to 100° C. and stirred at reflux for 8 hours. The resulting strands were filtered off using a nutsch-type filter and washed five times with 200 mL of deionized water until the conductivity of the water obtained from the washing was below 30 microSiemens. In an oven, the respectively obtained strands were heated to a temperature of 120° C. within 60 min and dried at that temperature for 240 min under air atmosphere. Then, the dried strands were heated to a temperature of 450° C. within 165 min and calcined at that temperature for 120 min under air atmosphere.

In the following table 1, the results of Comparative Example 1 (CE1), Comparative Example 2 (CE2) and Example 1 (E1) are shown.

TABLE 1

Characteristics of the moldings

| Strands | CE1 | CE2 | E1 |
|---|---|---|---|
| Zn content/weight-% | 1.1 | 1.2 | 1.6 |
| Ti content/weight-% | 1.4 | 1.2 | 1.4 |
| PO test/% [a] | 8.4 | 8.3 | 9.4 |
| PO test rate/bar/min [b] | 0.03 | 0.02 | 0.05 |
| Selectivity relative to propene [g]/% | 99.5 | n.d. [h] | 99.5 |
| Mechanical strength/N [c] | 14 | 5.3 | 15 |
| Water adsorption capacity/weight-% [d] | 7 | 12.2 | 11.6 |
| Pore volume/mL/g [e] | 1.3 | 1.4 | 1.5 |
| BET specific surface area/$m^2$/g [f] | 303 | 347 | 257 |

[a] determined as described in Reference Example 6 herein
[b] determined as described in Reference Example 6 herein
[c] determined as described in Reference Example 3 herein
[d] determined as described in Reference Example 7 herein
[e] determined as described in Reference Example 2 herein
[f] determined as described in Reference Example 1 herein
[g] the selectivity, after a time on stream of 500 h, was calculated as 100 times the ratio of moles of propylene oxide in the effluent stream divided by the moles of hydrogen peroxide (consumed) in the feed stream. The continuous reactions were carried out as described in Reference Example 9 herein
[h] not determined As shown in Table 1, the zinc content of the molding of the present invention was significantly higher (1.6 weight-%) than the zinc content of the prior art moldings (1.1 weight-%), although for preparing the strands of the invention, significantly less zinc acetate dihydrate per zeolitic material were employed (11.5%) compared with the prior art according to the comparative example 1 (18.4%). Further, with regard to the PO test as well as with regard to the PO test rate, the use of the strands according to the invention (E1) lead to significantly improved values compared to the Comparative Examples CE1 and CE2, i.e. they exhibit improved characteristics for the preferred use of the inventive strands since the higher the rate, the higher the catalyst activity since the propene starting material is consumed faster.

Furthermore, as shown in Table 1, E1 (autogenous conditions) shows significantly improved physical properties over CE2 (reflux conditions). In particular, the mechanical strength of CE2 is much lower (5.3 N for CE2 compared to 15 N for E1), highlighting that if reflux conditions are employed instead of the autogenous conditions of E1.2, then a product is obtained with inferior physical properties.

CITED LITERATURE

WO 2013/117536 A
WO 2015/010990 A

The invention claimed is:
1. A molding comprising zinc and a titanium-containing zeolitic material having framework type MWW, obtained by a process comprising:
   (i) providing a molding comprising a titanium-containing zeolitic material having framework type MWW;
   (ii) preparing an aqueous suspension comprising a zinc source and the molding comprising a titanium-containing zeolitic material having framework type MWW prepared in (i);
   (iii) heating the aqueous suspension prepared in (ii) under autogenous pressure to a temperature of the liquid phase of the aqueous suspension of from 100 to 200° C., thereby obtaining an aqueous suspension comprising a molding comprising zinc and a titanium-containing zeolitic material having framework type MWW; and

(iv) separating the molding comprising zinc and a titanium-containing zeolitic material having framework type MWW from the liquid phase of the suspension obtained in (iii);

wherein in (ii), the zinc source comprises a zinc compound which is soluble in water at a temperature and pressure of the liquid aqueous phase according to (iii).

2. The molding of claim 1, wherein the molding provided in (i) comprises the titanium-containing zeolitic material having framework type MWW and a binder, wherein in the molding provided in (i), a weight ratio of the titanium-containing zeolitic material having framework type MWW relative to the binder is from 1:1 to 9:1.

3. The molding of claim 2, wherein at least 99 wt. % of the molding provided in (i) consist of the titanium-containing zeolitic material having framework type MWW and the binder.

4. The molding of claim 1, wherein the molding provided in (i) has at least one of the following characteristics (1) to (3):
(1) a BET specific surface area of at least 300 m$^2$/g;
(2) a pore volume of at least 0.9 mL/g;
(3) a mechanical strength of from 5 to 10 N.

5. The molding of claim 1, wherein at least 99 wt. % of the titanium-containing zeolitic material having framework type MWW comprised in the molding provided in (i) consists of Ti, Si, O, and H, wherein the titanium-containing zeolitic material having framework type MWW comprised in the molding provided in (i) has a titanium content, calculated as elemental titanium, of from 0.1 to 5 wt. %, based on a total weight of the titanium-containing zeolitic material having framework type MWW.

6. The molding of claim 1, wherein the titanium-containing zeolitic material having framework type MWW comprised in the molding provided in (i) is in the form of a powder having a particle size distribution having a Dv10 value of from 1 to 10 micrometer, and a Dv90 value of from 12 to 200 micrometer.

7. The molding of claim 1, wherein the zinc source comprises at least one zinc salt soluble in water.

8. The molding of claim 1, wherein in the aqueous suspension prepared in (ii), a weight ratio of zinc comprised in the zinc source relative to the titanium-containing zeolitic material having framework type MWW comprised in the molding is from 0.005:1 to 0.1:1.

9. The molding of claim 1, wherein in the aqueous suspension prepared in (ii), a weight ratio of the titanium-containing zeolitic material having framework type MWW comprised in the molding relative to water is from 0.01:1 to 0.1:1.

10. The molding of claim 1, wherein in (iii), the suspension prepared in (ii) is heated to and kept at a temperature of the liquid phase of the aqueous suspension of from 110 to 175° C.

11. The molding of claim 1, wherein the process further comprises:
(v) drying the separated molding comprising zinc and a titanium-containing zeolitic material having framework type MWW obtained from (iv); and
(vi) calcining the dried molding comprising zinc and a titanium-containing zeolitic material having framework type MWW obtained from (v).

12. A molding comprising zinc and a titanium-containing zeolitic material having framework type MWW, wherein in the molding, a weight ratio of zinc relative to the titanium-containing zeolitic material having framework type MWW is from 0.005:1 to 0.1:1,
wherein the molding has a water absorption capacity of from 8 to 12 weight %.

13. The molding of claim 12, having at least one of the following characteristics:
a BET specific surface are of at least 200 to m$^2$/g;
a crystallinity of at least 50%;
a porosity of at least 0.9 mL/g;
a mechanical strength of from 9 to 23 N;
a PO test parameter of at least 8%.

14. A process for converting a hydrocarbon, comprising contacting the hydrocarbon with a catalyst comprising the molding of claim 1.

15. A process for converting a hydrocarbon, comprising contacting the hydrocarbon with a catalyst comprising the molding of claim 12.

16. The process of claim 15, wherein the hydrocarbon comprises an alkene, and the alkene is epoxidized in the presence of a solvent.

* * * * *